United States Patent [19]
Tilton, Jr.

[11] Patent Number: 5,503,623
[45] Date of Patent: Apr. 2, 1996

[54] INSTRUMENTATION FOR LAPAROSCOPIC INSERTION AND APPLICATION OF SHEET LIKE SURGICAL MATERIAL

[76] Inventor: Eugene B. Tilton, Jr., 513 Dorrington Blvd., Metairie, La. 70005

[21] Appl. No.: 407,409

[22] Filed: Mar. 17, 1995

[51] Int. Cl.$^6$ .................................................. A61B 17/00
[52] U.S. Cl. .......................... 604/13; 604/15; 604/11; 606/151
[58] Field of Search ........................ 128/898; 600/37; 602/57; 604/1, 2, 11–15, 17, 18, 27, 36, 43–45, 47–51, 59–64, 158–166, 171, 283, 264

[56] References Cited

U.S. PATENT DOCUMENTS

| | | | |
|---|---|---|---|
| 5,257,973 | 11/1993 | Villasuso | 604/49 |
| 5,263,927 | 11/1993 | Shlain | 604/13 |
| 5,295,952 | 3/1994 | Pietrafitta | 604/15 |
| 5,304,187 | 4/1994 | Green et al. | 604/13 X |
| 5,310,407 | 5/1994 | Casale | 604/59 |

*Primary Examiner*—Angela D. Sykes
*Assistant Examiner*—Stephen D. Huang

*Attorney, Agent, or Firm*—Pravel, Hewitt, Kimball & Krieger

[57] ABSTRACT

A method and apparatus for laparoscopic insertion and application of a sheet like material (such as an adhesion barrier) and like products enables the laparoscopic surgeon to utilize large and full size sheets of Interceed (3"×4") in abdominal (including pelvic) surgery. In laparoscopy surgery of the abdomen (including pelvis), all instrumentation and all surgical products must be introduced through "ports" consisting of valved sleeves or tubes. To properly and efficiently introduce and apply a large or full size sheet of sheet like material, the present invention provides a method and apparatus of grasping and furling the sheet and then unfurling, releasing and applying it after passage into the patient's abdominal cavity. The instrument consists of an operational grasping and furling portion which is rotated to furl the sheet like material. It is then "backloaded" or drawn into a tubular portion of the instrument, an inserter sheath for passage through the valved "port". Once the sheet like material is in the abdominal cavity it is unfurled. The grasping portion of the instrument provides for proper and easier alignment and then application of the unfurled sheet. Additional flexibility is achieved by an articulation mechanism which allows horizontal movement of the grasping/furling element to produce an angle in the instrument body.

12 Claims, 5 Drawing Sheets

INSTRUMENTATION FOR LAPAROSCOPIC INSERTION AND APPLICATION OF SHEET LIKE SURGICAL MATERIAL

BACKGROUND OF THE INVENTION

1. Field of the Invention

The present invention relates to a method and apparatus for inserting and applying large or full size sheets of surgical sheet like material (such as absorbable adhesion barrier) and other sheet like products in laparoscopic (endoscopic) surgery. Wherein the sheet of material is furled into a roll and held in a first delivery tube, then routed through a second tube or "port" for dispensing within the abdominal cavity.

2. General Background

Surgery performed within the pelvis and abdomen by means of laparoscopy consists of one or more entry "ports" in varying size. The majority of sizes is in the range of five (5) millimeters to fifteen (15) millimeters. Each port consists of a tube with proximal and distal ends. A valve structure on the proximal end of the port member allows instruments to be passed through the abdominal wall while maintaining appropriate intra-abdominal $CO_2$ pressure.

While instruments pass easily through the associated port member and its valve structure, cloth-like sheets of surgical material such as absorbable adhesion barrier and the like do not readily pass through the port. At this time, most laparoscopic surgeons cut such sheet like material into small pieces and shove it through the port, a more difficult insertion and also causing a less efficient and restricted application.

One example of surgical sheet like material is an absorbable adhesion barrier product manufactured by Johnson and Johnson Medical Inc. under the trademark "Interceed". Such an absorbable adhesion barrier is typically rectangular, measuring about three inches (3") wide and four inches (4") long. It is designed to be placed over surgical sites within the pelvis and abdomen.

Once placed on sites where surgery is performed, such a sheet like adhesion barrier helps in preventing development or recurrence of adhesions (a type of scarring) which can be painful and, in certain instances, dangerous. Currently, such a barrier (or sheet like material) is placed mostly by laparotomy (opened abdomen surgery). It is thus desirable to be able to efficiently place adhesion barrier sheets and similar surgical products into the abdomen laparoscopically, while making their proper placement easier and better. Placing anything laparoscopically into the abdomen is limited by the port member, from both a size standpoint and the valve structure, the latter being necessary to maintain intraabdominal pressure.

In surgeries where large areas are involved and application of sheet like products is desirable, the largest sheet of the product needed should be utilized. This provides not only faster and more efficient use of surgical time but a better and more stable application as well. The present instrument provides a system for laparoscopic use of large pieces or full size sheets of sheet like surgical material (such as absorbable adhesion barrier) and the like.

SUMMARY OF THE INVENTION

The present invention provides an instrumentation system for laparoscopic insertion and application of a surgical sheet like material such as absorbable adhesion barrier and the like. The method of the present invention comprises the grasping and furling of the sheet of material long wise along its border with a grasping instrument.

An instrument inserter tube or sheath is provided shorter in length then the grasping section. The grasping section extends through the inserter tube and protrudes beyond the distal end. The sheet of material is furled onto the grasping and furling section and drawn back ("backloaded") into the introducer.

A handle on the grasping instrument portion provides two finger grip positions that allow the surgeon to slide a cable connected to one of the grasping elements (a movable member) back and forth so as to fix or release the sheet like material.

A lever positioned on top of the grasping portion of the instrument moves backward and forward to cause a mechanical articulation of the grasping element once inside the patient's abdomen to aid in placement on the desired surface.

The proposed method of furling the sheet like material causes it to be rolled up lengthwise and in such a configuration it occupies very little space. The present instrument system which effects this idea is designed to allow efficient furling in a compact space, easy insertion or passage through the abdominal wall port, and then unfurling and applying to the surgical site.

In the initial step, a rectangular (e.g. 3"×4") piece of sheet like material is placed long wise in the grasping section of the instrument which is then rotated resulting in the sheet like material being furled. The next step is to slide this furled sheet backwards into the inserter sheath while it is being grasped. The backloaded, furled sheet, is now "ready". This sheet is held within a tube and the assembly is then passed through the laparoscopy port, a tubular member. The grasping portion is pushed forward through the port and into the patient's abdominal cavity. The sheet like material is then unfurled and applied, employing horizontal articulation if needed.

A gasket-seal is located at the connection between the instrument frame and inserter tube portion outside the abdomen. This prevents $CO_2$ gas in the abdomen from escaping.

There are a number of advantages of this instrument. The present invention provides a single intact reusable instrument, having a portion of the instrument being reusable and another portion being disposable. The present invention provides an entire disposable instrument with the ability to have prepackaged surgical products or simply providing the disposable instrument alone.

The same instrument system measurements could be altered in dimension so as to be utilized with other products with cloth-like and/or sheet like characteristics of different sizes and/or thickness.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 4:
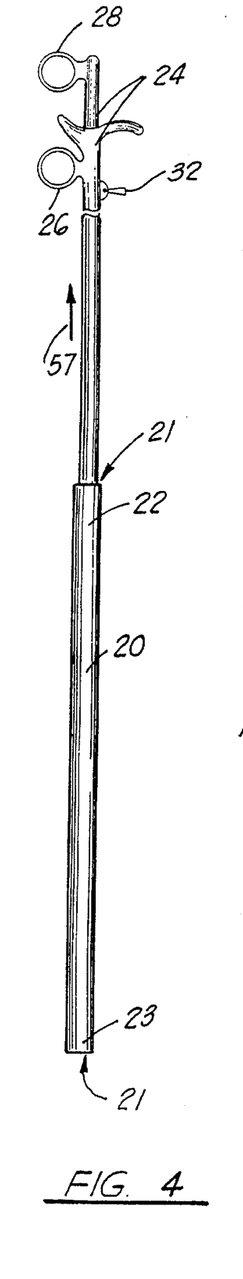
FIG. 4 is a side view of the preferred embodiment of the apparatus of the present invention showing the inserter instrument with a sheet of surgical material loaded in the distal end portion of the inserter instrument body.
Figure 5:
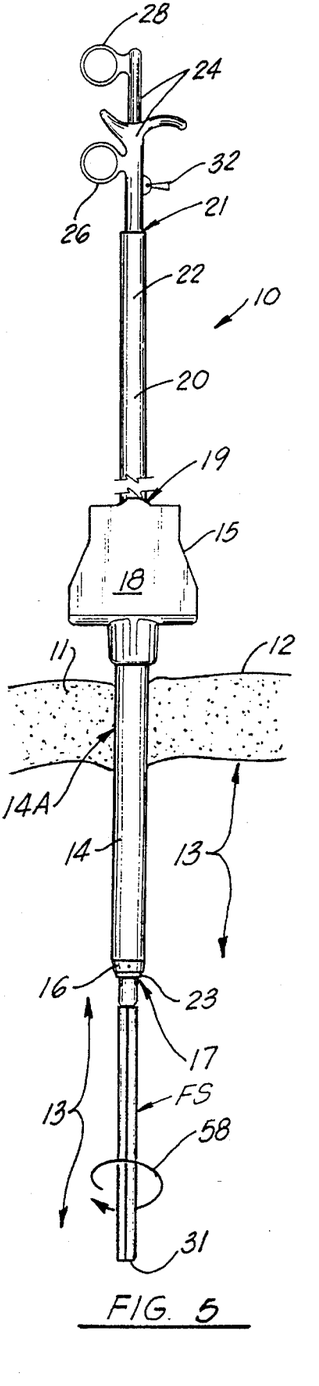
FIG. 5 is a schematic view illustrating placement of the apparatus of the present invention through a patient's abdominal wall and illustrating the method of the present invention.
Figure 6:
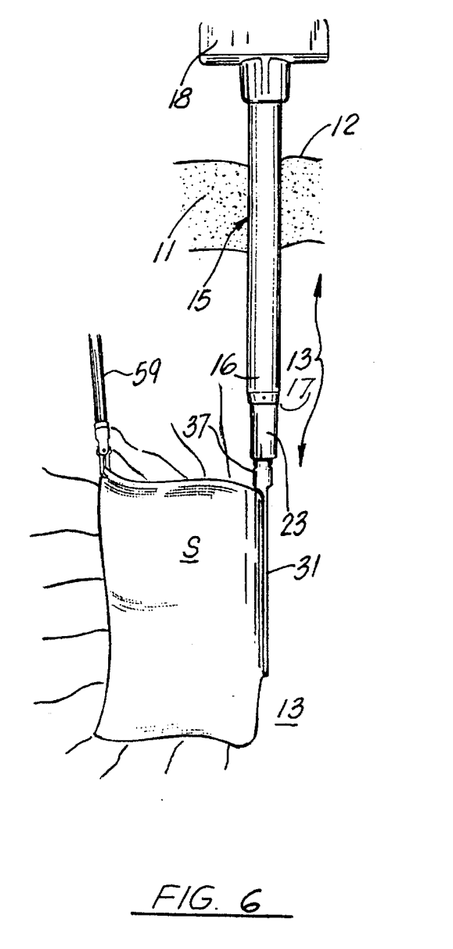
FIG. 6 is a side schematic view illustrating the method of the present invention.

FIGS. 1–6 illustrate the preferred embodiment of the apparatus of the present invention designated generally by the numeral 10. Laparoscopy instrument 10 includes an elongated structure that can be placed through the abdominal wall 11 of a patient as shown in FIG. 5. Also shown in FIGS. 5 and 6 is the patient's skin 12 and the abdominal cavity 13 into which an inserter instrument portion 24 of the instrument 10 will be placed.

Tubular port 14 extends through an opening 14A formed with the tubular member 14 through the patient's abdominal wall 11. This procedure of placing a port in the abdominal wall 11 is per se known. The tubular port 14 is a commercially available structure that includes a proximal end 15 and a distal end 16. The tubular port 14 provides an elongated open end cylindrical bore 17 so that the surgeon can communicate between the abdominal cavity 13 and the exterior of the patient. Cylindrical bore 17 is valved with valving member 18. The valving member 18 likewise provides a bore that is in communication with the cylindrical bore 17. Such a port 14 with its valving member 18 is sold commercially for use in laparoscopic surgery. In such a surgical procedure, it is well known in the art to inflate the abdomen to give the surgeon a better view of the surgical site.

An elongated inserter tube member 20 is sized and shaped to fit the internal bore 17 of the tubular port 14. The tubular member 20 provides a generally cylindrical outer surface that is of an external diameter that is substantially the same as or slightly smaller than the internal diameter cylindrical bore 17. The bore 19 of valving member 18 is also generally cylindrically shaped to conform to the outer surface of tubular member 20. The inserter tube member 20 has a proximal end 22 and a distal end 23. The tubular member 20 has a uniform cylindrical bore 21 that is open ended.

Figures 7, 8:
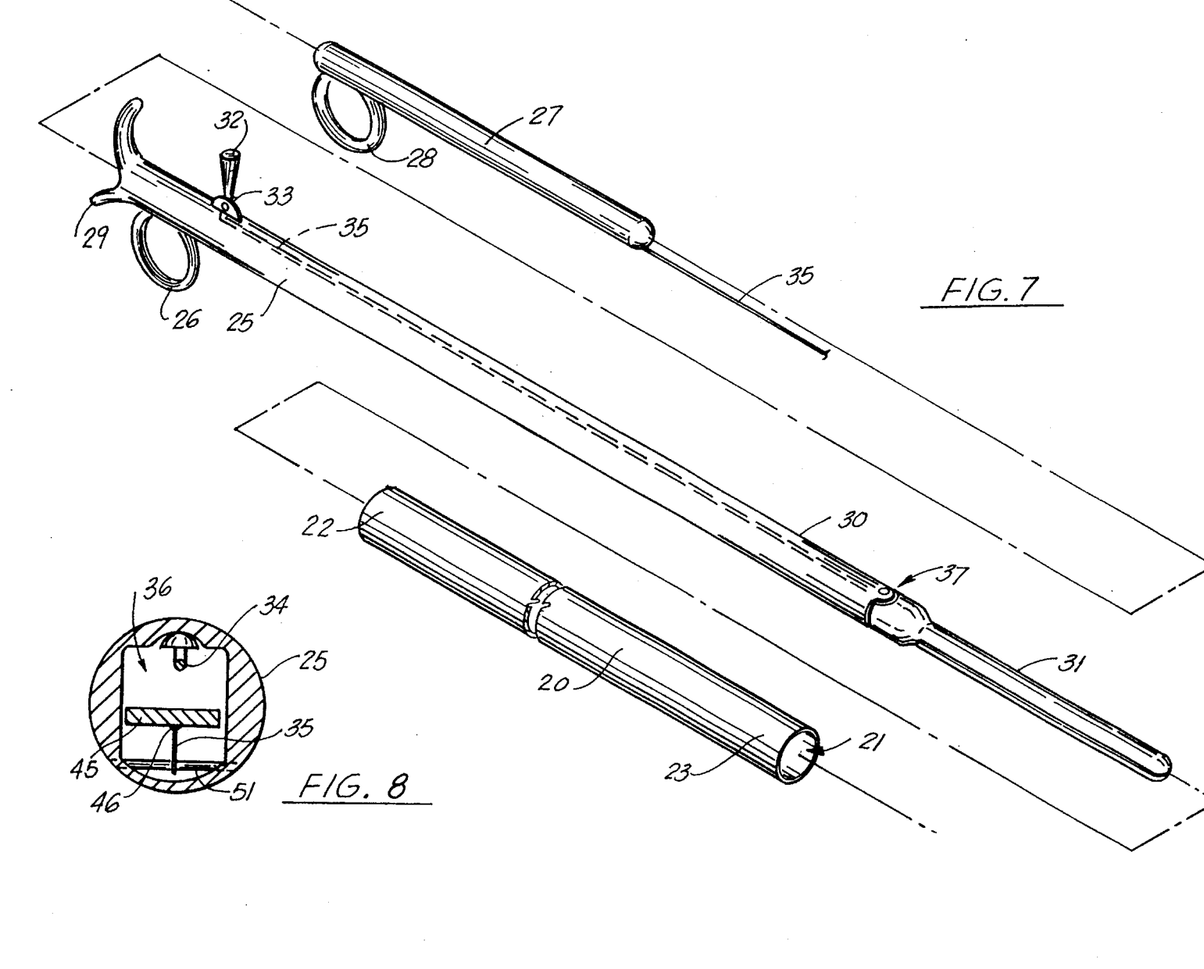
FIG. 7 is an exploded perspective view of the preferred embodiment of the apparatus of the present invention.
FIG. 8 is a sectional view of the preferred embodiment of the apparatus of the present invention.

An elongated inserter instrument 24 is comprised of external tubular member 25 and internal tubular member 27 (see FIG. 7). The external tubular member 25 has a handle 26 for manipulating it. Similarly, the internal tubular member 27 has a handle 28. The two handles 26, 28 are each in the form of a ring so that the surgeon can place one of his or her fingers through the handles 26, 28 for manipulating and sliding the member 27 relative to the member 25.

Figure 10:
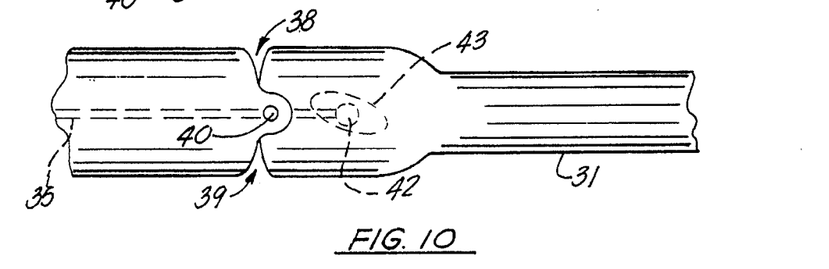
FIG. 10 is a top partial view of the preferred embodiment of the apparatus of the present invention.
Figure 11:
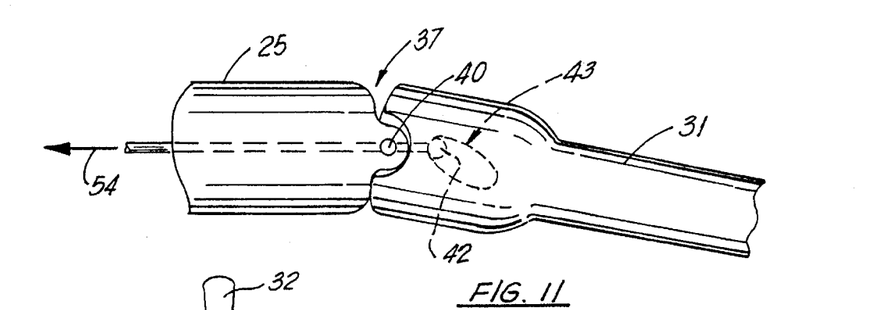
FIG. 11 is a top partial view of the preferred embodiment of the apparatus of the present invention illustrating an articulation of the distal end portion of the inserter instrument body.
Figure 12:
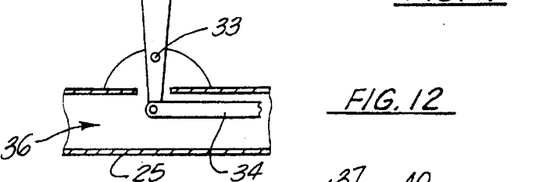
FIG. 12 is a fragmentary view of the lever portion of the preferred embodiment of the apparatus of the present invention.
Figure 13:
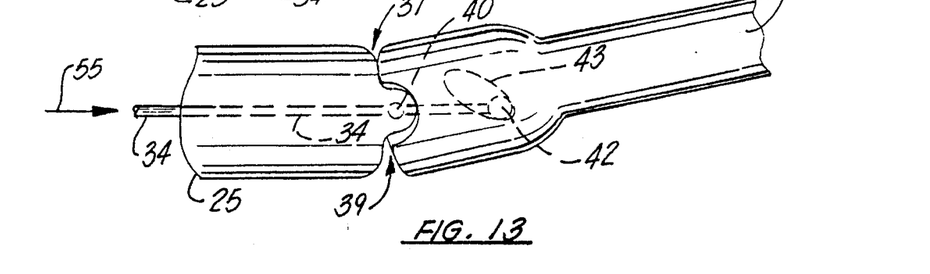
FIG. 13 is a fragmentary top view of the preferred embodiment of the apparatus of the present invention illustrating an articulation of the distal end portion of the inserter instrument.

External tubular member 25 has a proximal end 29 and a distal end 30. A grasping portion 31 is attached to the distal end 30 as shown in FIGS. 7 and 9–13. Lever 32 is pivotally attached to the proximal 29 end portion of external tubular member 25. Lever 32 is attached to pushrod 34 so that pivoting of lever 32 about its pivot 33 operates to extend or retract the pushrod relative to external tubular member 25. As will be described more fully hereinafter, the lever 32 is used to articulate grasping portion 31 into multiple angular positions relative to the central longitudinal axis of the external tubular member 25 as illustrated in FIGS. 10–11 and 13.

A cable 35 is attached to internal tubular member 27. The cable 35 extends through a longitudinal bore 36 within external tubular member 25. As will be described more fully hereinafter, the cable 35 is moved by pulling or pushing the internal tubular member 27 relative to the external tubular member 25 using handles 26, 28.

An articulating joint 37 forms a connection between external tubular member 25 and grasping portion 31. As shown in FIGS. 10–11 and 13, a pair of spaces 38, 39 are provided at articulating joint 37 for allowing the grasping portion 31 to angulate relative to the central longitudinal axis of external tubular member 25 as shown in FIGS. 10–11 and 13. A pinned connection 40 is formed at articulating joint 37 between the distal end 30 of external tubular member 25 and the grasping portion 31, allowing portion 31 to pivot upon tubular member 25.

Pushrod 34 includes an elbow section 41 that carries button 42. The button 42 fits in a recess 43. The recess 43 is formed on fixed member 44 of grasping portion 31. A moving member 45 is placed in close approximation to the fixed member 44. The moving member 45 travels away from the fixed member 44 when the cable 35 is pulled using lever 32. Cable 35 is attached at 46 to moving member 45. A coil spring 47 normally holds moving member 45 in face to face contact with fixed member 44. When the user pulls the internal tubular member 27 with handle 28, cable 35 pulls down on moving member 45. The coil spring 47 is positioned between underlying support 48 and moving member 45. A plurality of cable guides 49–51 are used to route the cable as shown in FIG. 9 to the under side of moving member 45 as shown.

Figure 9:
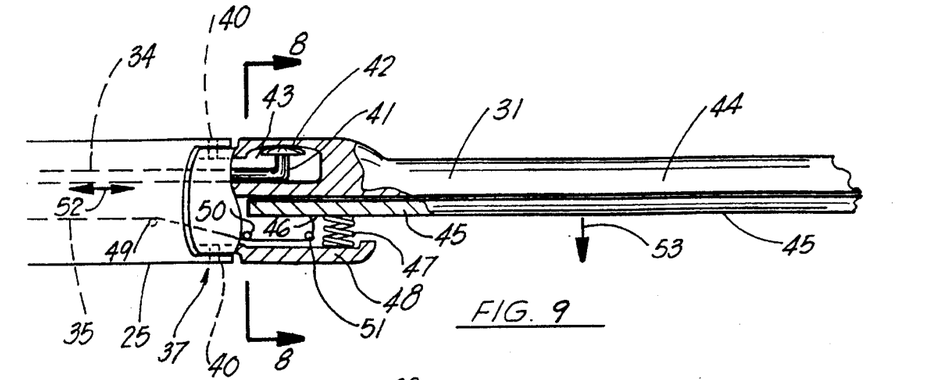
FIG. 9 is a fragmentary, partially cut-away view of the preferred embodiment of the apparatus of the present invention.

In FIG. 9, arrow 52 illustrates the movement of pushrod 34 fore and aft depending upon the surgeon manipulation of lever 32. In FIG. 10, the pushrod 34 is in a neutral position when the lever 32 is in an upright position, generally perpendicular to the central longitudinal axis of external tubular member 25 as shown in FIG. 7.

In FIG. 11, the surgeon has pulled the pushrod 34 as shown by arrow 54 in FIG. 11. This causes the button 42 to travel to the rear portion of recess 43 thereby pivoting grasping portion 31 relative to external tubular member 25. In FIG. 13, the surgeon has pushed the pushrod 34 using lever 32 as shown by the arrow 55. This causes the button 42 to travel to the forward portion of recess 43, thus pivoting the grasping portion 31 to opposite angular position of that shown in FIG. 11. In this fashion, the surgeon can articulate or pivot the grasping portion 31 relative to the central longitudinal axis of the external tubular member 25.

Figure 1:
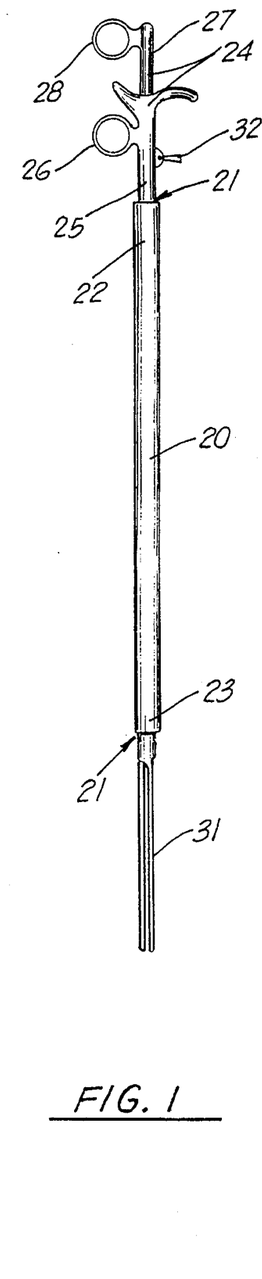
FIG. 1 is a side view of the preferred embodiment of the apparatus of the present invention.

In FIG. 9, arrow 53 designates a movement of moving member 45 away from fixed member 44. This is accomplished by pulling on the member 27 and its attached cable 35. Such a movement of member 45 in the direction of arrow 53 is used when either loading or releasing the sheet like member S to or from the instrument 10. Thus, the surgeon pulls the cable 35 to move member 45 away from member 44 producing a gap therebetween for application of an edge of sheet like member thereto. In FIG. 1, the gap has been formed between members 44 and 45 so that the surgeon can insert an edge of a sheet of material S into the gap formed between the members 44 and 45.

Figure 2:
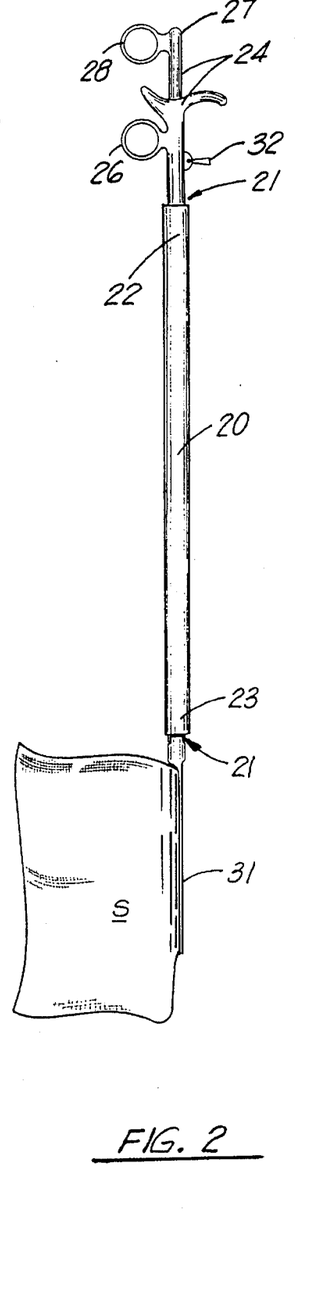
FIG. 2 is a side view of the preferred embodiment of the apparatus of the present invention illustrating the attachment of a sheet of surgical material thereto.
Figure 3:
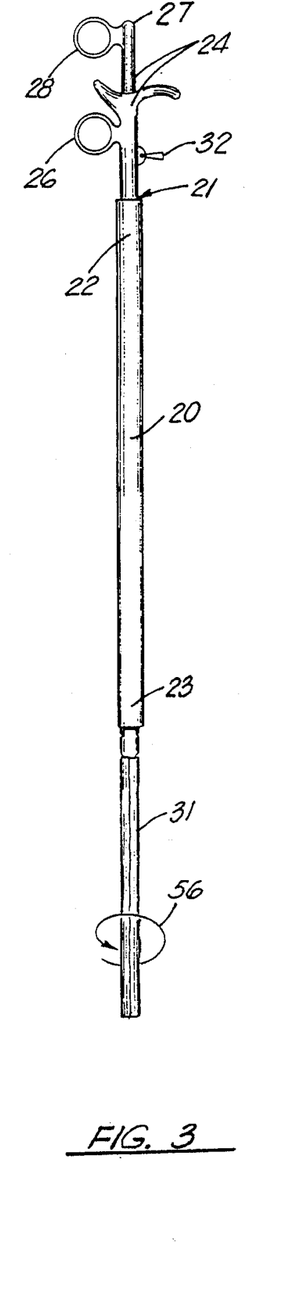
FIG. 3 is a side view of the preferred embodiment of the apparatus of the present invention showing the sheet of surgical material in a furled condition about the distal end of the inserter instrument body.

In FIG. 2, the sheet of material S has been placed in the gap between the member 44 and 45. The surgeon then releases the member 27 so that the spring 47 pushes the member 45 into close face to face contact with the member 44. This action clamps a selected edge of the sheet S between the members 44, 45 and allows the surgeon to the furl the sheet S about grasping portion 31 as shown by the arrow 56 in FIG. 3.

In FIG. 4, arrow 57 indicates that the furled sheet S has been with drawn into the bore of inserter tube 20. At this time, the sheet of material S has been furled about the grasping portion 31, and pulled into the bore 21. The combination of inserter tube 20, the sheet of material S, and the elongated inserter instrument 24 can now be inserted through tubular port member 14.

In FIG. 5, the surgeon uses port 14 to place the sheet of material S into the patient's abdominal cavity 13. This is accomplished by routing the distal end 23 of inserter tube 20 and the contained inserter instrument 24 through the bore 19 of valving member 18 and then through the bore 17 of tubular port member 14. The surgeon projects the inserter tube 20 into the abdominal cavity 13 until the distal end 23 is positioned close to the distal end 16 of tubular port member 14 as shown in FIG. 5. The surgeon then holds the inserter tube 20, fixing its position relative to the tubular port 14. In the next step of the method, the surgeon forces the elongated inserter instrument 24 into the abdominal cavity by moving the elongated inserter instrument 24 relative to both inserter tube 20 and port 14 so that the grasping portion 31 and the furled sheet FS of material are exposed inside the abdominal cavity 13.

In FIG. 5, the letters FS designate the furled sheet of material having been placed with the grasping portion 31 in the patient's abdominal cavity 13. The surgeon then rotates the elongated inserter instrument 24 as indicated by the arrow 58 in FIG. 5. This rotation unfurls the sheet of material S to the position shown in FIG. 6. A second port (such as member 14) can be used for placing a grasping instrument 59 into the abdominal cavity 13 for assisting the surgeon in application of the sheet of material S as illustrated in FIG. 6.

Figure 14:
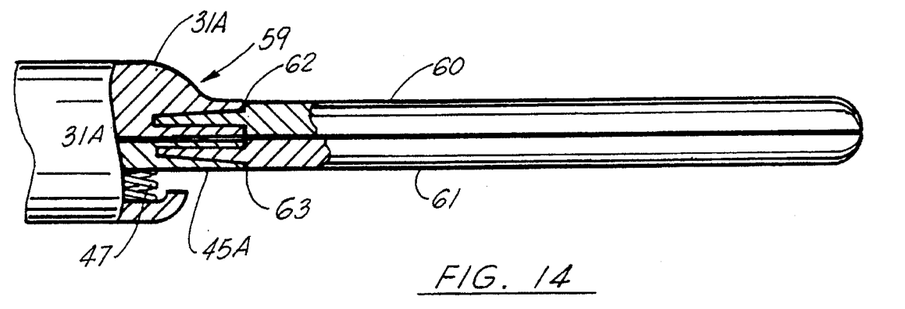
FIG. 14 is a partial, cut-away view of the distal end portion illustrating an alternative construction of the distal end portion of the inserter instrument.
Figure 15:
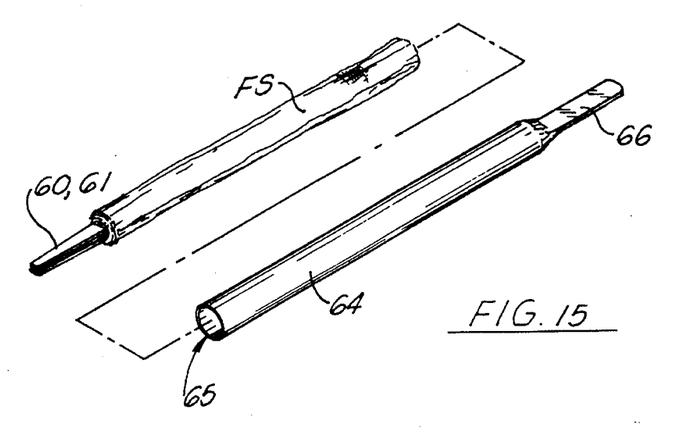
FIG. 15 is a fragmentary perspective view of the alternate construction of the distal end of the inserter instrument body.
Figure 16:
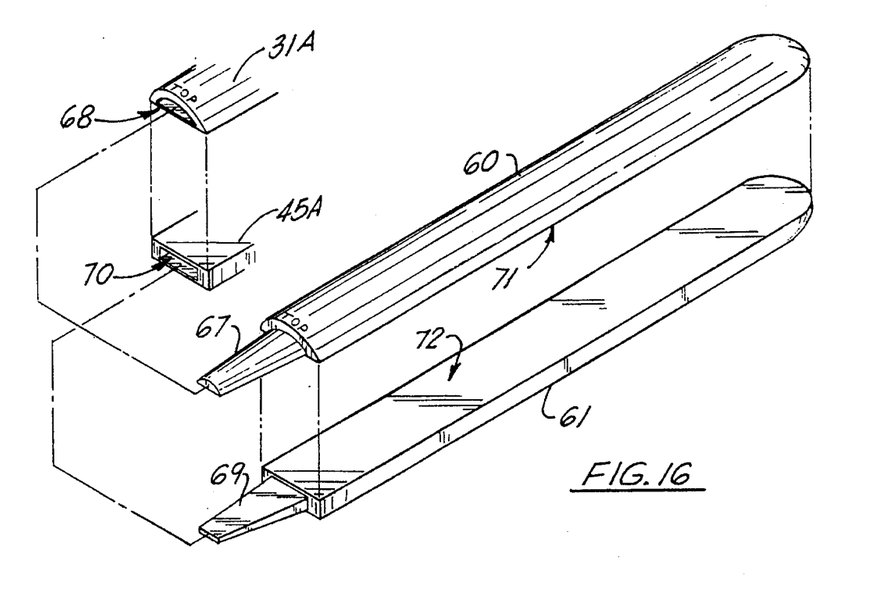
FIG. 16 is an exploded fragmentary view of the distal end portion of the inserter instrument body.

An alternate construction of the grasping portion as shown in FIGS. 14–16, designed as grasping portion 31A. Grasping portion 31A includes a removable connection designated as 59 in FIG. 14. Connection 59 is formed between grasping portion 31A and a pair of removable ends 60–61. A joint 62 is formed between removable end 60 and grasping portion 31A. A removable end 61 is connected at joint 63 to moving member 45A.

In FIG. 15, a prepackaged furled sheet FS of material is shown, furled about the removable ends 60, 61. The ends 60, 61 are pre-packaged with sheet S furled about the ends 60, 61. An edge of sheet S is grasped between ends 60, 61. The furled sheet FS and ends 60, 61 would be contained within the bore 65 of an elongated disposable sleeve 64. The sleeve 64 provides a pull tab 66 so that the user can install the furled sheet FS avoiding premature unfurling by simply holding and manipulating the sleeve 64. After the removable ends 60, 61 are installed by perfecting a connecting at the joint 62, 63 and backloading the furled sheet FS into sleeve 20, the surgeon then pulls on the pull tab 66 to remove the sleeve 64 so that the surgery can proceed.

In FIG. 16, removable end 60 provides a projection 67 that mates with a correspondingly shaped socket 68 of grasping portion 31A. Similarly, the moving member 45A provides a socket 70 that forms a connection with projecting portion 69 of moving member 61. The members 60, 61 each provide correspondingly sized and shaped flat surfaces 71, 72 that abut in face to face relation when the coil spring 47 forces members 45A, and 31 and 60, 61 together.

The connection between projections 67, 69 and sockets 68, can be a wedge lock or taper lock type connection to ensure a tight fit. In the embodiment of FIGS. 14–16, the removable ends 60, 61 and the furled sheet FS and sleeve 64 could be in a presterlized blister pack for example. The following table lists the parts numbers and parts descriptions as used herein and in the drawings attached hereto.

PARTS LIST

| Part Number | Description |
| --- | --- |
| 10 | laparoscopy instrument |
| 11 | abdominal wall |
| 12 | skin |
| 13 | abdominal cavity |
| 14 | tubular port |
| 15 | proximal end |
| 16 | distal end |
| 17 | cylindrical bore |
| 18 | valving member |
| 19 | bore |
| 20 | inserter tube |
| 21 | cylindrical bore |
| 22 | proximal end |
| 23 | distal end |
| 24 | inserter instrument |
| 25 | external tubular member |
| 26 | handle |
| 27 | internal tubular member |
| 28 | handle |
| 29 | proximal end |
| 30 | distal end |
| 31 | grasping portion |
| 31A | grasping portion |
| 32 | lever |
| 33 | pivot |
| 34 | pushrod |
| 35 | cable |
| 36 | longitudinal bore |
| 37 | articulating joint |
| 38 | space |

-continued

PARTS LIST

| Part Number | Description |
|---|---|
| 39 | space |
| 40 | pinned connection |
| 41 | elbow section |
| 42 | button |
| 43 | recess |
| 44 | fixed member |
| 45 | moving member |
| 45A | moving member |
| 46 | attachment |
| 47 | coil spring |
| 48 | underlying support |
| 49 | cable guide |
| 50 | cable guide |
| 51 | cable guide |
| 52 | arrow |
| 53 | arrow |
| 54 | arrow |
| 55 | arrow |
| 56 | arrow |
| 57 | arrow |
| 58 | arrow |
| 59 | grasping tool |
| 60 | removable end |
| 61 | removable end |
| 62 | joint |
| 63 | joint |
| 64 | sleeve |
| 65 | cylindrical bore |
| 66 | pull tab |
| 67 | projection |
| 68 | socket |
| 69 | projection |
| 70 | socket |
| 71 | flat surface |
| 72 | flat surface |
| S | sheet |
| FS | furled sheet |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of inserting a surgical sheet article into a patient's abdomen that has been inflated to afford a surgeon a better view of a surgical site within the patient's abdomen, comprising the steps of:

a) surgically forming a port through the patient's abdominal wall;

b) placement of said port including placing a first tubular member, having proximal and distal end portions and an elongated bore into the patient's abdomen, said proximal end having a valving member that valves a flow of gases through the bore and between the proximal and distal ends while the patient's abdomen has been inflated to afford a better view of a surgical site;

c) gripping the surgical sheet article with an inserter instrument having a pair of jaws for enabling said gripping;

d) furling the surgical sheet article into a roll about the jaws of the inserter instrument;

e) placing the furled surgical sheet article and the inserter instrument into a second, separate tubular member with a central longitudinal bore so that the second tubular member holds the surgical sheet article in the furled condition, wherein the surgical sheet article is furled about an axial line that coincides with a central longitudinal axis of the bore of the second tubular member;

f) inserting the second tubular member into the bore of the first tubular member, and through the valving member;

g) valving the flow of gases between the patient's abdominal cavity and the proximal end of the first tubular member with the valving member;

h) extending the distal end of the second tubular member below the distal end of the first tubular member and into the patient's abdominal cavity;

i) discharging the furled surgical sheet article from the distal end of the second tubular member and into the patient's abdominal cavity;

j) grasping the surgical sheet article after it extends completely through and exits the distal end of the second tubular member;

k) unfurling the surgical sheet article inside the patients abdominal cavity;

l) placing the unfurled sheet article in contact with a selected abdominal surface or structure.

2. The method of claim 1 further comprising the step between steps "e" and "f" of exiting the distal end of the first tubular member with the distal end of the second tubular member.

3. The method of claim 1 further comprising the step of furling the surgical sheet article about an inserter that fits the bore of the second tubular member.

4. The method of claim 1 further comprising the step of articulating the distal end of the second tube during placement of the unfurled surgical sheet article against an area of the surgical site wherein tissue is subject to formation of adhesions or scar tissue.

5. The method of claim 1 wherein the surgical sheet article is generally rectangular, and further comprising the step of maintaining the sheet edges generally parallel when the sheet is furled.

6. The method of claim 1 wherein the surgical sheet article is absorbable and further comprising the step of holding the sheet article against tissue that is subject to form adhesions or scar tissue until the sheet of material has absorbed some of the patient's body fluid.

7. The method of claim 1 wherein the surgical sheet article is oxidized regenerated cellulose and further comprising the step of allowing the sheet to eventually dissolve.

8. The method of claim 1 further comprising the step of articulating the gripped surgical sheet article with respect to the second tubular member during placement so that proper placement is enhanced.

9. A method of inserting a sheet of surgical adhesion barrier material into a pelvic area of a patient's abdomen that has been inflated to afford a surgeon a better view of a surgical site within the patient's abdomen, comprising the steps of:

a) surgically forming an opening in the patient's abdominal wall;

b) placing a first tubular member, having proximal and distal end portions and an elongated bore, through the surgically formed opening;

c) furling the sheet of material into a roll to define a furled sheet;

d) placing the furled sheet into the bore of a second tubular member so that the second tubular member holds the sheet in a furled condition, wherein the sheet is furled about an axial line that coincides with a central longitudinal axis of the second tubular member;

e) inserting the second tubular member and the contained furled sheet into the bore of the first tubular member;

f) valving flow gases at the proximal end of the first tubular member with a valve mounted at the proximal end of the first tubular member;

g) extending the distal end of the second tubular member into the patient's abdomen and adjacent tissue that is subject to form adhesions or scar tissue;

h) discharging the furled sheet from the second tubular member below the distal end of the first tubular member and into the patient's abdomen; and i) placing the sheet of material against the selected tissue; and j) articulating the sheet with respect to the second tubular member during placement so that proper placement is enhanced.

10. A method of inserting a surgical sheet article into a pelvic area of a patient's abdomen that has been expanded to afford a surgeon a better view of a surgical site within the patient's abdomen, comprising the steps of:

a) surgically forming an opening in the patient's abdominal wall;

b) placing a first tubular member, having proximal and distal end portions and an elongated bore, through the surgically formed opening;

c) gripping the surgical sheet article with an inserter instrument having a pair of active jaws that can be opened and closed by the surgeon for enabling said gripping and releasing;

d) furling the surgical sheet article into a roll about the jaws of the inserter to define a furled sheet;

e) placing the furled sheet into the bore of a second tubular member so that the second tubular member holds the sheet in a furled condition, wherein the furled sheet is furled about an axial line that coincides with a central longitudinal axis of the second tubular member;

f) placing the surgical sheet article against selected tissue by discharging the active jaws and article from the distal end of the second tubular member;

g) articulating the surgical sheet article with respect to the second tubular member during placement so that proper placement is enhanced; and h) releasing the sheet by opening the active jaws.

11. A method of inserting a surgical sheet article into a pelvic area of a patient's abdomen, comprising the steps of:

a) surgically forming an opening in the patient's abdominal wall;

b) placing a tubular member, having proximal and distal end portions and an elongated bore, through the surgically formed opening;

c) gripping the surgical sheet article with an inserter instrument having a pair of active jaws that can be opened and closed by the surgeon for enabling said gripping and releasing;

d) furling the surgical sheet article into a roll about the active jaws of the inserter to define a furled sheet;

e) placing the furled sheet into the bore of the tubular member so that the tubular member holds the surgical article sheet in a furled condition, wherein the sheet is furled about an axial line that coincides with a central longitudinal axis of the tubular member;

f) discharging the active jaws and surgical sheet article from the distal end portion of the tubular member and into the patient's abdomen;

g) placing the surgical sheet article against selected tissue; and h) releasing the sheet by opening the active jaws.

12. The method of claim 11 further comprising the step of articulating the sheet with respect to a second tubular member during placement so that proper placement is enhanced.

* * * * *